(12) United States Patent
Castelli

(10) Patent No.: US 6,345,196 B1
(45) Date of Patent: Feb. 5, 2002

(54) ELECTRODE FOR DETECTING AN ELECTRIC BIOLOGICAL SIGNAL, IN PARTICULAR AN ELECTROCARDIOGRAPHIC SIGNAL, AND ELECTROCARDIOGRAPH EMPLOYING SUCH AN ELECTRODE

(76) Inventor: Arrigo Castelli, Via Gerso, 3, CH-6900 Lugano (CH)

( * ) Notice: Subject to any disclaimer, the term of this patent is extended or adjusted under 35 U.S.C. 154(b) by 0 days.

(21) Appl. No.: 09/474,971

(22) Filed: Dec. 29, 1999

(30) Foreign Application Priority Data

Dec. 30, 1998 (IT) .......................................... TO98A1114

(51) Int. Cl.⁷ ............................................ A61B 5/0402
(52) U.S. Cl. ...................................... 600/509; 600/372
(58) Field of Search ................................ 600/372, 509, 600/382, 384; 607/153

(56) References Cited

U.S. PATENT DOCUMENTS

| | | | |
|---|---|---|---|
| 2,887,112 A | 5/1959 | Smith | 128/417 |
| 3,340,868 A | 9/1967 | Darling | 128/2.06 |
| 3,487,827 A | 1/1970 | Edmark | 128/2.06 |
| 3,746,004 A | 7/1973 | Jankelson | 128/410 |
| 4,166,453 A | 9/1979 | McClelland | 128/639 |
| 4,311,151 A | 1/1982 | Hagihara | 128/635 |
| 4,367,755 A | 1/1983 | Bailey | 128/798 |
| 4,375,219 A | 3/1983 | Schmid | 128/639 |
| 4,383,529 A | 5/1983 | Webster | 604/20 |
| 4,535,783 A | 8/1985 | Marangoni | 128/711 |
| 4,700,710 A | 10/1987 | Hoffman | 128/641 |
| 4,809,705 A | 3/1989 | Ascher | 128/710 |
| 5,928,141 A | 7/1999 | Castelli | 600/372 |

FOREIGN PATENT DOCUMENTS

| | | | |
|---|---|---|---|
| DE | 3040098 A1 | 6/1982 | A61B/5/04 |
| FR | 2 581 855 | 11/1986 | A61B/5/04 |
| WO | WO 80/01538 | 8/1980 | A61B/10/00 |
| WO | WO 97/30631 | 8/1997 | A61B/5/0408 |

OTHER PUBLICATIONS

European Search Report Application No. EP 99 12 5949 dated Apr. 4, 2000.

*Primary Examiner*—Scott M. Getzow
(74) *Attorney, Agent, or Firm*—Darby & Darby

(57) ABSTRACT

An electrode for detecting an electric biological signal, in particular an electrocardiographic signal, and having a metal conducting disk, and a rigid disk having holes and which is superimposed on and separated from the metal disk by a gap of constant thickness. A small amount of conducting liquid is poured on the electrode and settles inside all the holes and inside the gap to form a layer of conducting liquid superimposed on the metal disk and of constant thickness.

11 Claims, 1 Drawing Sheet

ELECTRODE FOR DETECTING AN ELECTRIC BIOLOGICAL SIGNAL, IN PARTICULAR AN ELECTROCARDIOGRAPHIC SIGNAL, AND ELECTROCARDIOGRAPH EMPLOYING SUCH AN ELECTRODE

The present invention relates to an electrode for detecting an electric biological signal, in particular an electrocardiographic signal, and to an electrocardiograph employing such an electrode. As is known, currently used instruments for detecting electrocardiographic signals comprise at least two external electrodes, which are placed on portions of the human body (e.g. the left and right arm) to detect electric biological signals present in the body as a result of cardiac activity.

BACKGROUND OF THE INVENTION

The electrodes are substantially flat, and are normally fixed to the human body by means of straps or adhesive means on the electrodes themselves, and, to improve electrical contact between each electrode and the human body, a thin layer of conducting gel is normally applied in between. Not being applied evenly to the electrode, however, the layer of conducting gel varies in thickness and fails to provide for an optimum distance between the electrode and the human body. On certain portions of the electrode, in fact, the layer of gel may be of such a thickness as to result in contact resistance unsuited to the characteristics of an instrument for detecting electrocardiographic signals.

Moreover, fastening means of the aforementioned type fail to provide for rigidly connecting the parts in electrical contact, and permit relative movements which may result in noise in the detected electric signal, even to the extent of impairing the results of the electrocardiogram.

SUMMARY OF THE INVENTION

It is an object of the present invention to provide an electrode for detecting an electric biological signal, in particular an electrocardiographic signal, designed to eliminate the drawbacks of known electrodes.

According to the present invention, there is provided an electrode for detecting an electric biological signal, in particular an electrocardiographic signal, as described in claim 1.

The present invention also relates to an electrocardiograph, as described in claim 11.

BRIEF DESCRIPTION OF THE DRAWINGS

A preferred, non-limiting embodiment of the present invention will be described, purely by way of example, with reference to the accompanying drawings, in which.

DETAILED DESCRIPTION OF THE INVENTION

Figure 1:
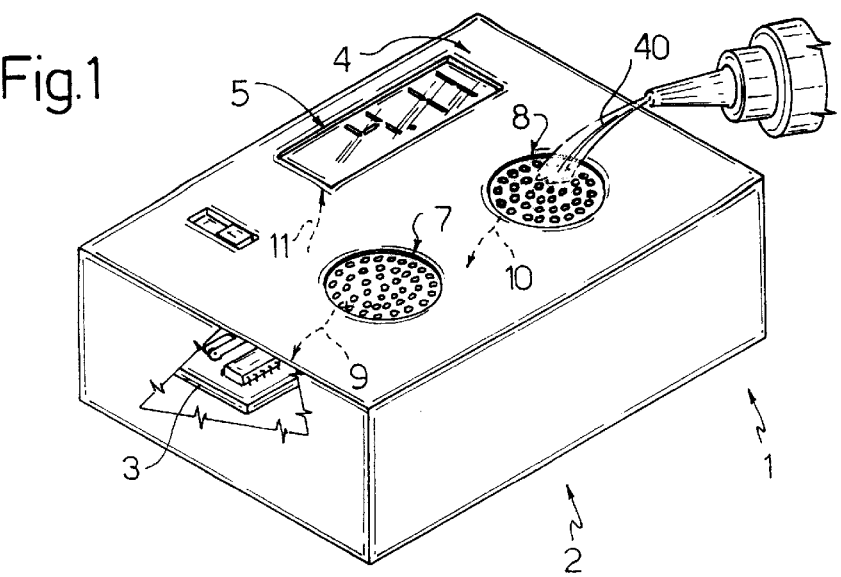
FIG. 1 shows a view in perspective of an instrument for detecting an electric biological signal, in particular an electrocardiographic signal, and featuring electrodes in accordance with the teachings of the present invention.

Number 1 in FIG. 1 indicates a portable instrument for detecting an electrocardiographic signal, and which comprises a substantially parallelepiped-shaped outer casing 2, and a known electronic processing circuit 3 (shown schematically) housed inside casing 2.

More specifically, casing 2 comprises a flat, rectangular face 4 on which are arranged a liquid crystal display 5, and two electrodes 7, 8 for detecting input signals. Rectangular face 4 is preferably made of insulating, in particular plastic, material.

Circuit 3 is supplied with an electric biological signal picked up from a patient (not shown), in particular an electrocardiographic signal from electrodes 7 and 8, and processes the signal to generate information shown on display 5 and indicating the cardiac activity of the patient (e.g. heart rate, electrocardiograph trace, etc.).

Electrodes 7, 8 communicate with circuit 3 by means of respective electric conductors 9, 10, and electronic circuit 3 communicates with display 5 via an electric line (bus) 11.

Figure 2:
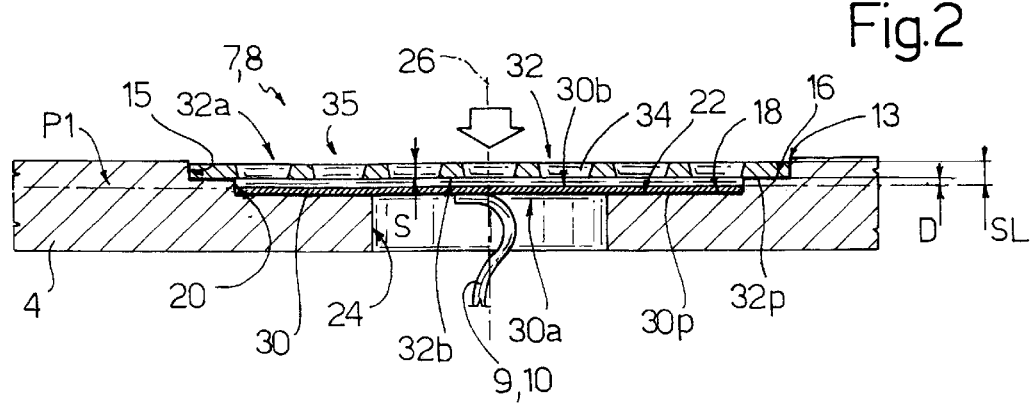
FIG. 2 shows a cross section of an electrode in accordance with the present invention.

FIG. 2 shows a cross section of an electrode 7, 8.

More specifically, face 4 comprises a circular first recessed seat 13 defined by a cylindrical lateral wall 15, and by an annular bottom wall 16 in which is formed a circular second recessed seat 18 coaxial with first recessed seat 13. Second recessed seat 18 is defined by a cylindrical lateral wall 20, and by a bottom wall 22 in which is formed a cylindrical through hole 24 coaxial with an axis 26.

Each electrode 7, 8 comprises a flat, disk-shaped metal conductor 30 (e.g. made of chloridized silver) housed inside second recessed seat 18 with a peripheral edge 30p of the conductor fixed (e.g. glued) to bottom wall 22, so that flat metal conductor 30 has a flat circular first face 30a facing face 4 and inwards of casing 2, and a flat circular second face 30b facing outwards of casing 2.

The thickness of conductor 30 (measured along axis 26) is less than the height (also measured along axis 26) of cylindrical lateral wall 20; and conductor 30 communicates electrically with electric conductor 9, 10 housed partly inside hole 24.

Figure 3:
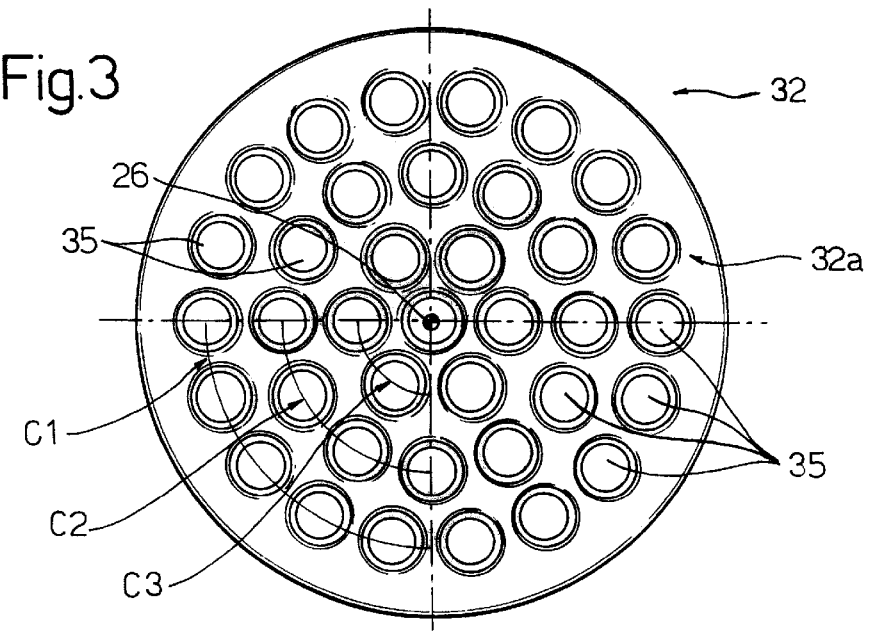
FIG. 3 shows a front view of the FIG. 2 electrode.

Each electrode 7, 8 also comprises a flat insulating disk 32 (FIGS. 2 and 3) housed inside first recessed seat 13 with a peripheral edge 32p of the disk fixed to annular wall 16. Flat insulating disk 32 is made of rigid plastic insulating material (e.g. nylon), and is defined by a first face 32a facing outwards of the casing, and by a second face 32b facing inwards of casing 2, and which therefore faces, and is separated by a distance D from, face 30b of flat metal conductor 30.

A cylindrical gap 34, of height D and the same diameter as recessed seat 13, is thus formed between metal conductor 30 and flat insulating disk 32.

Flat insulating disk 32 comprises:

a first number of through holes 35 (e.g. eighteen) arranged along a first circumference C1 coaxial with axis 26;

a second number of through holes 35 (e.g. twelve) arranged along a second circumference C2 coaxial with and inwards with respect to circumference C1;

a third number of through holes 35 (e.g. six) arranged along a third circumference C3 coaxial with and inwards with respect to circumference C2; and a central through hole 35.

More specifically, each through hole 35 is truncated-cone-shaped with a cross section in the form of an isosceles trapezium and tapering from first face 32a to second face 32b of disk 32, i.e. from the outside of electrode 7, 8 towards flat metal conductor 30. Each hole 35 has a mean diameter of about 1.5 mm.

Gap 34 communicates externally of electrode 7, 8 through holes 35.

As stated, flat insulating disk 32 —preferably made of plastic material—forms a rigid flat structure which is substantially undeformable in a direction (shown by the arrow in FIG. 2) crosswise to the plane P1 containing flat conductor 30.

In actual use, a small amount of a conducting liquid 40, in particular chlorinated water, is poured onto each electrode 7, 8 (FIG. 1), and penetrates holes 35 to fill gap 34 and settle evenly on conductor 30. The particular section of holes 35 (tapering inwards of electrode 7, 8) helps the conducting liquid 40 to enter and also provides a certain extent of drawing of the conducting liquid 40 into gap 34.

A layer of conducting liquid 40 communicating with the conducting liquid inside holes 35 is thus formed in gap 34. More specifically, inside each hole 35, the conducting liquid forms a column of liquid extending the full height of hole 35 to a higher level substantially coplanar with face 32a.

Inside each electrode 7,8, a layer of conducting liquid of thickness SL is thus formed, comprising the liquid inside gap 34 and holes 35, and of a thickness D+S, where D is the height of gap 34, and S the thickness of flat insulating disk 32. Since disk 32 is substantially undeformable (in particular, noncompressible) and the deflection of disk 32 towards gap 34 totally negligible with respect to the loads on electrode 7,8, thickness SL is substantially constant. In actual use, a portion of the human body, in particular the tip of a finger, is placed on face 32a of disk 32 of electrode 7, 8, so that the portion of the human body communicates electrically (ohmic contact) with the conducting liquid inside holes 35, and therefore with conducting disk 30 via the layer of conducting liquid of constant thickness SL. An optimum distance between conductor 30 and the human body is thus ensured by a layer of liquid of a given constant thickness, thus ensuring a contact resistance suitable for the characteristics of the electrocardiographic signal detecting instrument.

Electrode 7,8 also provides for a rigid arrangement of the parts in electrical contact, by preventing relative movements of the parts, and, hence, for preventing the formation of noise in the electric signal picked up by the electrode.

Clearly, changes may be made to the device as described and illustrated herein without, however, departing from the scope of the present invention. For example, as opposed to chlorinated water, ohmic contact may be obtained using any other liquid solution having similar conducting characteristics.

What is claimed is:

1. An electrode for detecting an electric biological signal, in particular an electrocardiographic signal, characterized by comprising:

a substantially flat conductor (30); and a rigid, substantially flat structure (32) facing said substantially flat conductor (30) and having a number of through holes (35) for containing a conducting fluid (40); said electrode (7, 8) receiving said conducting fluid (40), which is distributed in said holes (35) to form a layer of conducting fluid superimposed on said flat conductor (30) and of substantially constant thickness (SL) even when a body portion is placed contacting the rigid, substantially flat structure (32) to form an ohmic contact with said flat conductor (30).

2. An electrode as claimed in claim 1, wherein said rigid, substantially flat structure (32) is substantially undeformable in a direction crosswise to the plane (P1) containing said flat conductor (30).

3. An electrode as claimed in claim 1, wherein said rigid, substantially flat structure (32) is spaced (D) with respect to said flat conductor (30) to form a gap (34) communicating with said holes (35); said gap (34) receiving said conducting fluid (40) from said holes (35) to form a layer of conducting fluid distributed evenly on said flat conductor (30).

4. An electrode as claimed in claim 1, wherein the holes (35) have a cross section decreasing from the outside of the electrode (7, 8) towards the flat conductor (30).

5. An electrode as claimed in claim 4, wherein said holes (35) are truncated-cone-shaped.

6. An electrode as claimed in claim 4, wherein said holes (35) each have a cross section in the form of an isosceles trapezium.

7. An electrode as claimed in claim 4, wherein the holes (35) have a mean diameter of about 1.5 mm.

8. An electrode as claimed in claim 1, wherein said rigid structure (32) is disk-shaped.

9. An electrode as claimed in claim 1, wherein said flat conductor (30) is disk-shaped.

10. An electrode as claimed in claim 1, wherein said holes (35) are arranged in concentric circles (C1, C2, C3).

11. An electrocardiograph comprising a pair of electrodes (7, 8) for detecting an electrocardiographic signal; a processing circuit (3) for processing said signal; and display means (5) for displaying the results of processing said signal; characterized in that each of said electrodes comprises:

a substantially flat conductor (30); and a rigid, substantially flat structure (32) facing said substantially flat conductor (30) and having a number of through holes (35) for containing a conducting fluid (40); said electrode (7, 8) receiving said conducting fluid (40), which is distributed in said holes (35) to form a layer of conducting fluid superimposed on said flat conductor (30) and of substantially constant thickness (SL) even when a body portion is placed contacting the rigid, substantially flat structure (32) to form an ohmic contact with said flat conductor (30).

* * * * *